US006699849B1

(12) United States Patent
Loftsson et al.

(10) Patent No.: US 6,699,849 B1
(45) Date of Patent: *Mar. 2, 2004

(54) CYCLODEXTRIN COMPLEXES OF BENZODIAZEPINES

(75) Inventors: Thorsteinn Loftsson, Reykjavik (IS); Mar Masson, Reykjavik (IS); Einar Stefansson, Reykjavik (IS)

(73) Assignee: Cyclops, ehf., Reykjavik (IS)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,185

(22) Filed: Feb. 16, 1999

Related U.S. Application Data

(60) Provisional application No. 60/075,544, filed on Feb. 23, 1998.

(51) Int. Cl.$^7$ .................. A61K 31/715; A61K 31/55; C08B 30/18; C08B 37/16; C07D 243/14
(52) U.S. Cl. .................. 514/58; 514/219; 514/220; 536/46; 536/103; 540/569
(58) Field of Search .................. 540/569, 58; 514/219, 514/220; 536/46, 103

(56) References Cited

U.S. PATENT DOCUMENTS

| | | | |
|---|---|---|---|
| 5,134,127 A | 7/1992 | Stella et al. | 514/58 |
| 5,324,718 A | 6/1994 | Loftsson | 514/58 |
| 5,376,645 A | 12/1994 | Stella et al. | 514/58 |
| 5,472,954 A | 12/1995 | Loftsson | 514/58 |

FOREIGN PATENT DOCUMENTS

WO      94/02518      2/1994

OTHER PUBLICATIONS

Loftsson and Brewster, *Pharm. Technol. Eur.*, 9(5), 26–34 (1997). (May, 1997).
Loftsson and Brewster, *J. Pharm. Sci.*, 85(10), 1017–1025 (1996). (Oct., 1996).
Rajewski and Stella, *J. Pharm. Sci.*, 85 (11), 1142–1169 (1996); (Nov., 1996).
Irie and Uekama, *J. Pharm. Sci.*, 86(2), 147–162 (1997). (Feb., 1997).
Stella and Rajewski, *Pharm. Res.*, 14(5), 556–567 (1997).
Loftsson, *Pharmazie*, 53, 733–740 (1998).
Frömming and Szejtli, *Cyclodextrins in Pharmacy*, Kluwer Academic Publishers, Dordrecht, The Netherlands, pp. 105–107 (1994).
Loftsson and Ólafsson, *Int. J. Dermatol.*, 37, 241–246 (1998).
Loftsson and Stefánsson, *Drug. Dev. Ind. Pharm.*, 23 (5), 473–481 (1997).
Loftsson, Másson and Stefánsson, "Cyclodextrins as Permeation Enhancers", *Proceedings of the 17$^{th}$ Pharmaceutical Technology Conference and Exhibition*, vol. 2, Dublin, pp. 313–324 (Mar. 24–26, 1998).
Schwartz, Rhodes and Cooper, *J. Pharm. Sci.*, 66, 994–997 (1977). (Apr., 1976).
Loftsson and Bodor, *Acta Pharm. Nord.*, 1, 185–194 (1989). (Issue No. 4).
Loftsson and Sigudardóttir, "Cyclodextrins as skin penetration enhancers,", in J. Szejtli and Szente (eds)., *Proceedings of the Eighth International Symposium on Cyclodextrins*, Kluwer Academic Publishers, pp. 403–406 (1996).
Roth, Eger and Troschütz, *Pharmaceutical Chemistry*, vol. 2: Drug Analysis, Ellis Horwood, pp. 308–309 (1991).
Gerecke, *Br. J. Clin. Pharmac.*, 11S–16S (1983).
Oh et al, *International Journal of Pharmaceutics*, 73, pp. 23–31 (1991).
*Pharmaceutical Chemistry*, vol. 2: Drug Analysis, ed. H.J. Roth et al., pp. 302–311; 496–513; 518–525; 546–547; 580–581; 590–591; 594–597; 659–673; published by Ellis Horwood, London (1988).
*Chemical Stability of Pharmaceuticals, A Handbook for Pharmacists*, Second Edition, ed. Kenneth A. Connors et al, pp. 257–263; 675–684; 764–773; published by Wiley–Interscience; John Wiley & Sons, New York (1986).
Stenlake, *Foundations of Molecular Pharmacology*, vol. 1, Medicinal and Pharmaceutical Chemistry, pp. 512–513, published by The Athlone Press, University of London (1979).
Junquera et al, *J. Org. Chem.*, 63, pp. 4349–4358 (1998).(WWW publ. : Jun. 11, 1998).
Li et al, *Journal of Pharmaceutical Sciences*, 87, No. 12, pp. 1535–1537 (1998).(12/98).
Krishnamoorthy et al., "Complexation of Weak Acids and Bases with Cyclodextrins: Effects of Substrate Ionization and the Estimation and Interpretation of Association Constants," *International J. of Pharmaceutical Advances*, 1(3), 330–343 (Jan., 1996).
Loftsson et al. (I), "Effects of 2–Hydroxypropyl–β–cyclodextrin on the Aqueous Solubility of Drugs and Transdermal Delivery of 17–β–Estradiol," *Acta Pharm. Nord.*, 1(4), 185–194 (1989).
Menard et al., "Studies on the Effect of pH, Temperature and ring Size on the Complexation of Phenytoin with Cyclodextrins," *Pharm. Acta Helv.*, 63(11), 303–308 (1988).

(List continued on next page.)

Primary Examiner—James O. Wilson
Assistant Examiner—L E Crane
(74) Attorney, Agent, or Firm—Burns, Doane, Swecker & Mathis, L.L.P.

(57) ABSTRACT

Methods for enhancing the complexation efficiency of a drug with cyclodextrin and for enhancing the availability of a drug following administration of a cyclodextrin-drug complex.

50 Claims, 5 Drawing Sheets

OTHER PUBLICATIONS

Loftsson et al. (II), "The Influence of Water–Soluble Polymers and pH on Hydroxylpropyl–β–cyclodextrin Complexation of Drugs," *Drug Development and Industrial Pharmacy*, 22(5), 401–405 (1996); see also HCAPlus abstract.

Selva et al., "Study of the Salts of Organic Hydroxy Acids of the Terfenadine β–Cyclodextrin Complex in Solution by Mass Spectrometry," *Journal of Mass Spectrometry*, 30(1), 219–220 (1995).

Fenyvesi et al., "Enhancement of the Drug Solubilizing Capacity of Hydroxypropyl–β–cyclodextrin by Ternary Complex Formation," in *The 7th Cyclodextrin Symposium*, T. Osa (ed.), Business Center for Academic Societies Japan, Tokyo, Japan, 1994, pp. 414–418.

Vikmon et al., "Terfenadine/Cyclodextrin/Hydroxyacid Multicomponent Complexes," in *The 7th Cyclodextrin Symposium*, T. Osa (ed.), Business Center for Academic Societies Japan, Tokyo, Japan, 1994, pp. 480–483.

CYCLODEXTRIN COMPLEXES OF BENZODIAZEPINES

CROSS-REFERENCE TO RELATED APPLICATION

This application claims the priority of United States Provisional Patent Application No. 60/075,544, filed Feb. 23, 1998, incorporated by reference herein in its entirety and relied upon.

BACKGROUND OF THE INVENTION

1. Field of the Invention

The invention relates to methods for enhancing the complexation of a heterocyclic drug with cyclodextrin and to methods for enhancing the availability of a heterocyclic drug following administration of a cyclodextrin-drug complex.

2. Background Art

Cyclodextrins are a group of structurally related saccharides which are formed by enzymatic cyclization of starch by a group of amylases termed glycosyltransferases. Cyclodextrins are cyclic oligosaccharides, consisting of (α-1,4)-linked α-D-glucopyranose units, with a somewhat lipophilic central cavity and a hydrophilic outer surface. The most common naturally occurring cyclodextrins are α-cyclodextrin, β-cyclodextrin and γ-cyclodextrin consisting of 6, 7 and 8 glucopyranose units, respectively. Of these three derivatives, β-cyclodextrin appears to be the most useful pharmaceutical complexing agent due to its cavity size, availability, low cost and other properties.

The natural cyclodextrins, in particular β-cyclodextrin, have limited aqueous solubility and their complex formation with lipophilic drugs often results in precipitation of solid drug-cyclodextrin complexes. Thus, the solubility of β-cyclodextrin in water is only about 18.5 mg/ml at room temperature. This low aqueous solubility is, at least partly, associated with strong intramolecular hydrogen bonding in the cyclodextrin crystal lattice. Substitution of any of the hydrogen bond-forming hydroxyl groups, even by hydrophobic moieties such as methoxy groups, will increase the aqueous solubility of β-cyclodextrin. In addition, since these manipulations frequently produce large numbers of isomeric products, chemical modification can transform the crystalline cyclodextrins into amorphous mixtures increasing their aqueous solubility.

Cyclodextrin derivatives of current pharmaceutical interest include the hydroxypropyl derivatives of α-, β- and γ-cyclodextrin, sulfoalkylether cyclodextrins such as sulfobutylether β-cyclodextrin, alkylated cyclodextrins such as the randomly methylated β-cyclodextrin, and various branched cyclodextrins such as glucosyl- and maltosyl-β-cyclodextrin (T. Loftsson and M. E. Brewster, "Cyclodextrins as pharmaceutical excipients", *Pharm. Technol. Eur.*, 9(5), 26–34 (1997); T. Loftsson and M. E. Brewster, "Pharmaceutical applications of cyclodextrins. I. Drug solubilization and stabilization", *J. Pharm. Sci.* 85(10), 1017–1025 (1996); R. A. Rajewski and V. J. Stella, "Pharmaceutical applications of cyclodextrins. 2. In vivo drug delivery", *J. Pharm. Sci.* 85(11), 1142–1169 (1996); T. Irie and K. Uekama, "Pharmaceutical applications of cyclodextrins. 3. Toxicological issues and safety evaluation", *J. Pharm. Sci.*, 86(2), 147–162 (1997); V. J. Stella and R. A. Rajewski, "Cyclodextrins: their future in drug formulation and delivery", *Pharm. Res.*, 14(5), 556–567 (1997); T. Loftsson, "Increasing the cyclodextrin complexation of drugs and drug bioavailability through addition of water-soluble polymers", *Pharmazie*, 53, 733–740 (1998)).

Preparation of Cyclodextrin Inclusion Complexes

In aqueous solutions, cyclodextrins form complexes with many drugs through a process in which the water molecules located in the central cavity are replaced by either the whole drug molecule, or more frequently, by some lipophilic portion of the drug structure. Once included in the cyclodextrin cavity, the drug molecules may be dissociated through complex dilution, by replacement of the included drug by some other suitable molecule (such as dietary lipids or bile salts in the GI tract) or, if the complex is located in close approximation to a lipophilic biological membrane (such as the mucosal membrane of the GI tract), the drug may be transferred to the matrix for which it has the highest affinity. Importantly, since no covalent bonds are formed or broken during the drug-cyclodextrin complex formation, the complexes are in dynamic equilibrium with free drug and cyclodextrin molecules (R. A. Rajewski and V. J. Stella, "Pharmaceutical applications of cyclodextrins. 2. In vivo drug delivery", *J. Pharm. Sci.* 85(11), 1142–1169 (1996)).

Various methods have been applied to the preparation of drug-cyclodextrin complexes (T. Loftsson and M. E. Brewster, "Pharmaceutical applications of cyclodextrins. I. Drug solubilization and stabilization", *J. Pharm. Sci.* 85(10), 1017–1025 (1996); T. Loftsson and M. E. Brewster, "Cyclodextrins as pharmaceutical excipients", *Pharm. Technol. Eur.*, 9(5), 26–34 (1997)). In solution, the complexes are usually prepared by addition of an excess amount of the drug to an aqueous cyclodextrin solution. The suspension formed is equilibrated (for periods of up to one week at the desired temperature) and then filtered or centrifuged to form a clear drug-cyclodextrin complex solution. Since the rate determining step in complex formation is often the phase to phase transition of the drug molecule, it is sometimes possible to shorten this process by formation of supersaturated solutions through sonication followed by precipitation. For preparation of the solid complexes, the water is removed from the aqueous drug-cyclodextrin solutions by evaporation or sublimation, e.g. spray-drying or freeze-drying. Other methods can also be applied to prepare solid drug-cyclodextrin complexes including kneading methods, co-precipitation, neutralization and grinding techniques. In the kneading method, the drug is added to an aqueous slurry of a poorly water-soluble cyclodextrin such as β-cyclodextrin. The mixture is thoroughly mixed, often at elevated temperatures, to yield a paste which is then dried. This technique can frequently be modified so that it can be accomplished in a single step with the aid of commercially available mixers which can be operated at temperatures over 100° C. and under vacuum. The kneading method is a cost-effective means for preparing solid cyclodextrin complexes of poorly water-soluble drugs. Co-precipitation of a cyclodextrin complex through addition of organic solvent is also possible. Unfortunately, the organic solvents used as precipitants can interfere with complexation which makes this approach less attractive than the kneading method. However, we have discovered that some organic solvents under some specific conditions, e.g. 10% (v/v) aqueous acetic acid solution, can enhance the complexation. Solid complexes of ionizable drugs can sometimes be prepared by the neutralization method wherein the drug is dissolved in an acidic (for basic drugs) or basic (for acidic drugs) aqueous cyclodextrin solution. The solubility of the drug is then lowered through appropriate pH adjustments (i.e. formation of the unionized drug) to force the complex out of solution. Finally, solid drug-cyclodextrin complexes can be formed by the grinding of a physical mixture of the drug and cyclodextrin and then heating the mixture in a sealed container to 60 to 90° C.

Methods for Enhancing Cyclodextrin Complexation

For a variety of reasons including cost, production capabilities and toxicology, the amounts of cyclodextrin which can be used in most drug formulations is limited (T. Loftsson and M. E. Brewster, "Cyclodextrins as pharmaceutical excipients", *Pharm. Technol. Eur.*, 9(5), 26–34 (1997); T. Loftsson, "Increasing the cyclodextrin complexation of drugs and drug bioavailability through addition of water-soluble polymers", *Pharmazie*, 53, 733–740 (1998)).

If one drug molecule (D) forms a complex with one cyclodextrin molecule (CD), then the complexation efficiency ([D-CD]/[CD]) will be equal to the intrinsic solubility of the drug ($S_0$) times the stability constant of the drug-cyclodextrin complex ($K_C$). In aqueous cyclodextrin solutions saturated with drug, the concentration of free drug ([D]) is approximately equal to $S_0$. Thus, increased complexation efficiency can be obtained by either increasing $S_0$ or by increasing $K_C$ or by increasing both simultaneously. Addition of organic solvents, such as ethanol, to the aqueous complexation media can result in enhanced complexation efficiency through increase in $S_0$. Drug ionization can increase the complexation efficiency through increase in $S_0$. Addition of certain low molecular weight acids, such as acetic, citric, malic, or tartaric acid, to aqueous complexation media can enhance cyclodextrin solubilization of basic drugs through increase in $S_0$ (i.e. salt formation, pH changes and lowering melting point) and/or increase in the apparent $K_C$. Water-soluble polymers can increase the complexation efficiency through increase in the apparent $K_C$. Furthermore, it is often possible to enhance cyclodextrin complexation even further by using several different methods simultaneously to enhance the cyclodextrin complexation. Pharmaceutical applications of these and other methods have been reviewed (See T. Loftsson, "Increasing the cyclodextrin complexation of drugs and drug bioavailability through addition of water-soluble polymers", *Pharmazie*, 53, 733–740 (1988); T. Loftsson and M. E. Brewster, "Cyclodextrins as pharmaceutical excipients", *Pharm. Technol. Eur.*, 9(5), 26–34 (1997); T. Loftsson and M. E. Brewster, "Pharmaceutical applications of cyclodextrins. I. Drug solubilization and stabilization", *J. Pharm. Sci.* 85(10), 1017–1025 (1996)).

Permeability of Drugs Through Biological Membranes

The cyclodextrin molecules are relatively large (molecular weight ranging from almost 1000 to over 1500), with a hydrated outer surface, and under normal conditions, cyclodextrin molecules will only permeate biological membranes with considerable difficulty (R. A. Rajewski and V. J. Stella, "Pharmaceutical applications of cyclodextrins. 2. In vivo drug delivery", *J. Pharm. Sci.* 85(11), 1142–1168 (1996); T. Irie and K. Uekama, "Pharmaceutical applications of cyclodextrins. 3. Toxicological issues and safety evaluation", *J. Pharm. Sci.* 86(2), 147–162 (1997); K.-H. Frömming and J. Szejtli, *Cyclodextrins in pharmacy*, Kluwer Academic Publishers, Dordrecht, The Netherlands, 1994; T. Loftsson and J. H. Ólafsson, "Cyclodextrins: new drug delivery systems in dermatology", *Int. J. Dermatol.*, 37, 241–246 (1998); T. Loftsson and E. Stefánsson, "Effect of cyclodextrins on topical drug delivery to the eye", *Drug Dev. Ind. Pharm.* 23(5), 473–481 (1997)). It is generally recognized that cyclodextrins act as true carriers by keeping the hydrophobic drug molecules in solution and deliver them to the surface of the biological membrane, e.g. skin, mucosa or the eye cornea, where they partition into the membrane. The relatively lipophilic membrane has low affinity for the hydrophilic cyclodextrin molecules and therefore they remain in the aqueous membrane exterior, e.g. the aqueous vehicle system, salvia or the tear fluid. Conventional penetration enhancers, such as alcohols and fatty acids, disrupt the lipid layers of the biological barrier. Cyclodextrins, on the other hand, act as penetration enhancers by increasing drug availability at the surface of the biological barrier. Furthermore, addition of water-soluble polymer, such as polyvinylpyrrolidone, apparently increase even further the availability of the drug molecules at the surface of the biological membrane resulting in enhanced drug bioavailability (T. Loftsson, "Increasing the cyclodextrin complexation of drugs and drug bioavailability through addition of water-soluble polymers", *Pharmazie*, 53, 733–740 (1998); T. Loftsson, M. Másson and E. Stefánsson, "Cyclodextrins as Permeation enhancers", *Proceedings of the 17th Pharmaceutical Technology Conference and Exhibition*, Volume 2, Dublin, Mar. 24–26, 1998, pp. 313–324).

OBJECTS AND SUMMARY OF THE INVENTION

Enhancing Complexation Efficiency

It is possible to enhance the cyclodextrin (CD) complexation efficacy, or efficiency, of drugs (D), and other "guest" molecules, by either increasing the apparent stability constant ($K_C$) of the drug-cyclodextrin complex (D-CD) or increasing the apparent intrinsic solubility ($S_0$) of the drug. For example, $K_C$ can be increased by addition of water-soluble polymers to the aqueous complexation media and $S_0$ can be increased by ionization of the drug molecule, as described previously. However, increased complexation efficiency by itself does not necessarily result in increased drug availability in the aqueous complexation media or increased drug availability from solid drug-cyclodextrin complexes. On the other hand, if the drug-cyclodextrin complexes are prepared under conditions which ensure enhanced complexation and if the complexation efficiency decreases upon administration, then enhanced drug availability will be observed. Thus, the present invention involves: i) enhancement of the complexation efficiency and ii) reduction of the complexation efficiency after administration. For example, it is possible to enhance the complexation efficiency of many ionizable drugs by preparing the complexes at a pH where the drug is ionized but obtain decreased efficiency upon administration due to pH changes and consequent decreased ionization. One example of such a drug is phenytoin (pKa 8.1). Its solubility in water at room temperature (25° C.) is only 18 µg/ml at pH 5 and 32 µg/ml at pH 8 (P. A. Schwartz, C. T. Rhodes and J. W. Cooper, "Solubility and ionisation characters of phenytoin", *J. Pharm. Sci.*, 66, 994–997 (1977)). Addition of 25% (w/v) 2-hydroxypropyl-β-cyclodextrin to the aqueous solutions increases the solubility of phenytoin to 5.0 mg/ml at pH 5 and 6.4 mg/ml at pH 8, which is 280- and 200-fold solubility enhancement, respectively. Although the apparent stability constant ($K_C$) of the phenytoin-cyclodextrin complex is much larger for the drug in the unionized form than for the anionic form, it is possible to obtain much higher total solubility by increasing the apparent intrinsic solubility ($S_0$) of the drug (T. Loftsson and N. Bodor, "Effects of 2-hydroxypropyl-β-cyclodextrin on the aqueous solubility of drugs and transdermal delivery of 17β-estradiol", *Acta Pharm. Nord.*, 1, 185–194 (1989)). However, if the pH 8.0 solution was placed in an environment which would decrease the pH from 8 to 5 (e.g. topical application to the skin), then a supersaturated solution would be formed which would result in enhanced drug availability (e.g. it would result in enhanced transdermal drug delivery). Other means to enhance $S_0$ include reversible derivation (e.g. prodrug formation) of the guest molecule and addition of certain low molecular weight acids. The value of $K_C$ can, for example, be increased by addition of certain low molecular weight acids, by addition of water-soluble polymers to the aqueous complexation media or by using mixed solvent systems such as aqueous 10% (v/v) acetic acid. For example, addition of the polymers and heating in an autoclave (to 120–140° C. for 20–40 minutes) does not only increase the complexation but it has also been shown to enhance transdermal and transcorneal drug delivery (T. Loftsson and A. M. Sigurdardottir, "Cyclodextrins as skin penetration enhancers", in J. Szejtli and L. Szente (Eds.) *Proceedings of the Eighth International Symposium on Cyclodextrins*, Kluwer Academic Publishers, 1996, pp. 403–406; T. Loftsson and E. Stefansson, "Effect of cyclodextrins on topical drug delivery to the eye", *Drug Devel. Ind. Pharm.*, 23(5), 473–481 (1997)). As shown in Table 1 below, it is not enough to add the polymers to the complexation medium. Addition of polymers to the unheated vehicles did not enhance the transdermal delivery of enalaprilat. However, heating the vehicles after addition of the polymers resulted in significant enhancement. The effect of the polymers on the transdermal delivery of enalaprilat can, at least partly, be explained by decreased complexation efficiency (i.e. decrease in $K_C$) at the skin surface.

TABLE 1

The effect of heating on transdermal delivery of enalaprilat from 10% (w/v) HPβCD solutions at pH 5.0 containing 2.5% enalaprilat in a suspension. The concentration of dissolved enalaprilat was between 2.0 and 2.3% (w/v).

| Donor phase | Flux (mg h$^{-1}$ cm$^{-2}$) | | |
|---|---|---|---|
| (w/v per cent) | Un-heated | Heated | Ratio |
| HPβCD | 18 ± 2 | — | — |
| HPβCD, 0.25% PVP | 16 ± 6 | 23 ± 7 | 1.4 |
| HPβCD, 0.10% HPMC | 14 ± 3 | 37 ± 12 | 2.6 |

In one aspect of the present invention there is provided a method for enhancing the complexation efficacy, i.e. efficiency, of a drug with cyclodextrin, said drug having a structure comprising at least one heterocyclic ring having a total of from 4 to 7 ring atoms, of which from 1 to 3 are hetero ring atoms, each of said hetero ring atoms being selected from nitrogen, oxygen and sulfur, said ring being a cyclic imine, enamine, lactone, lactam, thiolactam, anhydride, imide, hemiacetal or hemiketal, said method comprising subjecting said drug to chemically reversible ring-opening so that at least a portion (at least 0.1% by weight) thereof is in ring-opened form, and complexing said drug with cyclodextrin.

In a related aspect of the invention, there is provided a method for enhancing the complexation efficiency of a drug with cyclodextrin, said drug having a structure comprising at least one heterocyclic ring having a total of from 4 to 7 ring atoms, of which from 1 to 3 are hetero ring atoms, each of said hetero ring atoms being selected from nitrogen, oxygen and sulfur, said ring being a cyclic imine, enamine, lactone, lactam, thiolactam, anhydride, imide, hemiacetal or hemiketal, said method comprising complexing said drug with cyclodextrin in an aqueous medium under conditions which effect chemically reversible ring-opening of at least a portion (at least 0.1% by weight) of said drug.

In another aspect of the invention, there is provided a method for enhancing the availability of a drug following administration of a cyclodextrin-drug complex to a warm-blooded animal in need of same, said drug having a structure comprising at least one heterocyclic ring having a total of from 4 to 7 ring atoms of which from 1 to 3 are hetero ring atoms, each of said hetero ring atoms being selected from nitrogen, oxygen and sulfur, said ring being a cyclic imine, enamine, lactone, lactam, thiolactam, anhydride, imine, hemiacetal or hemiketal, said method comprising complexing said drug with cyclodextrin in an aqueous medium under conditions which effect chemically reversible ring-opening of at least a portion (at least 0.1% by weight) of said drug to enhance the complexation efficiency, followed by administering the cyclodextrin-drug complex thus obtained to said animal under conditions which reduce the complexation efficiency.

In still another aspect, the present invention provides a method for enhancing the availability of a basic drug (i.e. a proton acceptor) following administration of a cyclodextrin-drug complex to a warm-blooded animal in need of same, said basic drug having a structure comprising at least one heterocyclic ring having a total of from 4 to 7 ring atoms, of which from 1 to 3 are hetero ring atoms, each of said hetero ring atoms being selected from nitrogen, oxygen and sulfur, said ring being a cyclic imine, enamine, lactone, lactam, thiolactam, anhydride, imide, hemiacetal or hemiketal, said method comprising subjecting said basic drug to complexation in an aqueous medium at a pH level below the pKa+2 value of said basic drug to enhance the complexation efficiency, followed by administering the cyclodextrin-drug complex thus obtained to said animal under conditions which reduce the complexation efficiency.

In yet another aspect, the present invention provides a method for enhancing the availability of an acidic drug following administration of a cyclodextrin-drug complex to a warm-blooded animal in need of same, said acidic drug having a structure comprising at least one heterocyclic ring having a total of 4 to 7 ring atoms, of which from 1 to 3 are hetero ring atoms, each of said hetero ring atoms being selected from nitrogen, oxygen and sulfur, said ring being a cyclic imine, enamine, lactone, lactam, thiolactam, anhydride, imide, hemiacetal or hemiketal, said method comprising subjecting said acidic drug to complexation in an aqueous medium at a pH level above the pKa-2 value of said acidic drug to enhance the complexation efficiency, followed by administering the cyclodextrin-drug complex thus obtained to said animal under conditions which reduce the complexation efficiency.

DETAILED DESCRIPTION OF THE INVENTION

Figure 1:
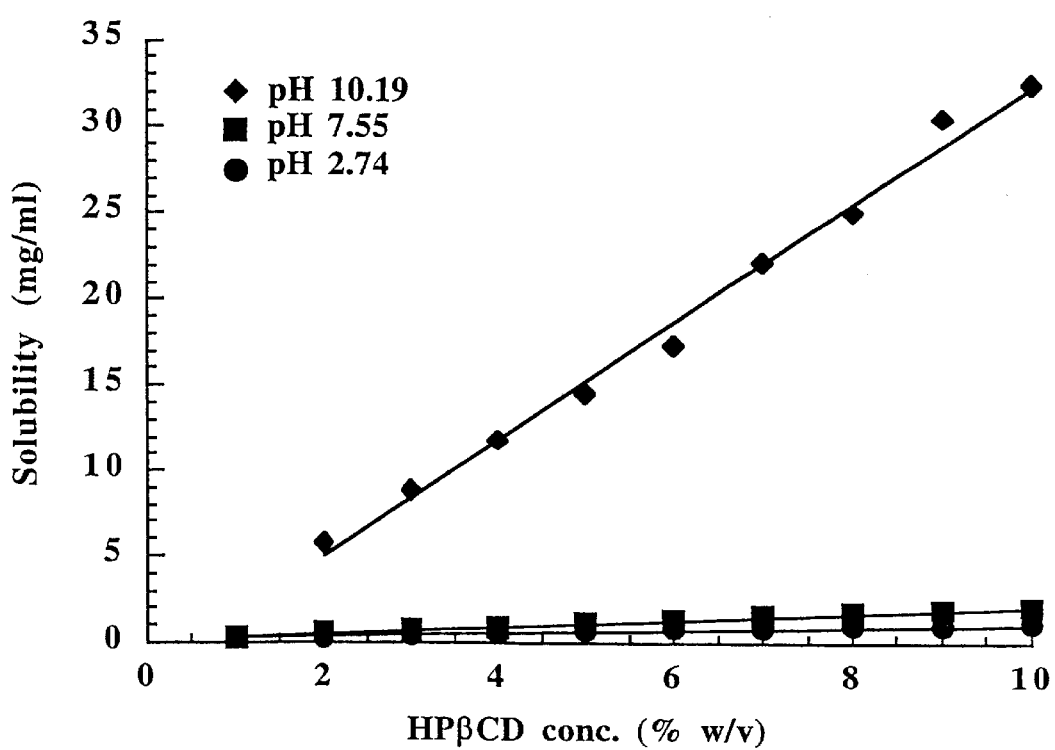
FIG. 1 is a graph illustrating the effect of pH on the phase-solubility of phenytoin (pKa 8.1) in aqueous hydroxypropyl-β-cyclodextrin (HPβCD) solutions at 25° C. at pH 10.19 (♦); pH 7.55 (■) and pH 2.74 (●)

The expression "cyclodextrin" as used herein means α- β- or γ-cyclodextrin or a derivative thereof. The following table (Table 2) lists α-cyclodextrin derivatives, β-cyclodextrin derivatives and γ-cyclodextrin derivatives for use in the present invention.

heterocyclic ring which is a cyclic imine, enamine, lactone, lactam, thiolactam, anhydride, imide, hemiacetal or hemiketal.

Especially desirable drugs for use in accord with the present invention are benzodiazepines. Benzodiazepines contain a benzene ring fused with a diazepine ring which is a 7-membered ring with nitrogen atoms in positions 1 and 4. By way of example, the chemical name of alprazolam is 8-chloro-1-methyl-6-phenyl-4H-s-triazolo[4,3-a][1,4] benzodiazepine, the chemical name of midazolam is 8-chloro-6-(2-fluorophenyl)-1-methyl-4H-imidazo[1,5-a] [1,4]benzodiazepine and that of triazolam is 8-chloro-6-(o-chlorophenyl)-1-methyl-4H-s-triazolo[4,3-a][1,4] benzodiazepine. Thus, all of these compounds have the 1,4-benzodiazepine structure with a double bond between nitrogen atom number 4 and carbon atom number 5 (which gives the molecule a cyclic imine structure). The benzodiazepines are cyclic imines. They are all basic, i.e. they are proton acceptors. Preferred benzodiazepines for use herein are alprazolam, brotizolam, chlordiazepoxide, clobazam, clonazepam, clorazepam, demoxazepam, flumazenil, flurazepam, halazepam, midazolam, nordazepam,

TABLE 2

Some of the currently available cyclodextrins obtained by substitution of the OH-groups located on the edge of the cyclodextrin ring. Since both the number of substituents and their location will affect the physicochemical properties of the cyclodextrin molecules, such as their aqueous solubility and complexing abilities, each derivative listed should be regarded as a group of closely related cyclodextrin derivatives.

| Type | α-Cyclodextrin derivatives | β-Cyclodextrin derivatives | γ-Cyclodextrin derivatives |
|---|---|---|---|
| Alkylated: | Methyl | Methyl | Methyl |
|  |  | Ethyl |  |
|  | Butyl | Butyl | Butyl |
|  |  |  | Pentyl |
| Hydroxylalkylated: |  | Hydroxyethyl | Hydroxyethyl |
|  | 2-Hydroxypropyl | 2-Hydroxypropyl | 2-Hydroxypropyl |
|  |  | 2-Hydroxybutyl |  |
| Esterified: | Acetyl | Acetyl | Acetyl |
|  |  | Propionyl |  |
|  |  | Butyryl |  |
|  | Succinyl | Succinyl | Succinyl |
|  |  | Benzoyl |  |
|  |  | Palmityl |  |
|  |  | Toluenesulfonyl |  |
| Esterified and alkylated: |  | Acetyl methyl |  |
|  |  | Acetyl butyl |  |
| Branched: | Glucosyl | Glucosyl | Glucosyl |
|  | Maltosyl | Maltosyl | Maltosyl |
| Ionic: | Carboxymethyl ether | Carboxymethyl ether | Carboxymethyl ether |
|  |  | Carboxymethyl ethyl |  |
|  | Phosphate ester | Phosphate ester | Phosphate ester |
|  |  | 3-Trimethylammonium-2-hydroxypropyl ether |  |
|  |  | Sulfobutyl ether |  |
| Polymerized: | Simple polymers | Simple polymers | Simple polymers |
|  | Carboxymethyl | Carboxymethyl | Carboxymethyl |

Particularly preferred cyclodextrins for use herein are hydroxypropyl-β-cyclodextrin, β-cyclodextrin sulfobutyl ether, the branched β-cyclodextrins (especially glucosyl-β-cyclodextrin and maltosyl-β-cyclodextrin), β-cyclodextrin, hydroxypropyl-γ-cyclodextrin and γ-cyclodextrin.

In preferred aspects of the present invention, the drug for use herein is one having a structure comprising at least one heterocyclic ring. The heterocyclic ring generally has a total of 4 to 7 ring atoms, of which from 1 to 3 are hetero ring atoms. While each hetero ring atom can be nitrogen, oxygen or sulfur, heterocycles having at least one nitrogen or oxygen ring atom are preferred. Preferably, the drug has at least one medazepam, diazepam, nitrazepam, oxazepam, midazepam, lorazepam, prazepam, quazepam, triazolam, temazepam and lorazolam. Especially preferred are midazolam, alprazolam, clonazepam, lorazepam and triazolam.

Another group of preferred drugs for use herein consists of the barbituric acid derivatives. The barbituric acids contain a 2,4,6-trihydroxypyrimidine (also called 2,4,6-trioxohexahydropyrimidine) ring in their structure, a 6-member ring with nitrogen in positions 1 and 3. Thus, the chemical name of barbital is 5,5-diethyl-2,4,6(1H,3H,5H)-pyrimidinetrione and that of phenobarbital is 5-ethyl-5-phenyl-2,4,6(1H,3H,5H)-pyrimidinetrione. The barbituric acids can be characterized as cyclic amides or lactams (cyclic amides are called lactams) or imides (which are nitrogen analogues of cyclic anhydrides). Barbituric acids are weak acids. Preferred barbituric acid derivatives are barbital, butobarbital, amobarbital, phenobarbital, aprobarbital, secobarbital, crotylbarbital, cyclobarbital, phenobarbital, hexobarbital, methylphenobarbital, thiopental, isopropylbromallylbarbituric acid, cyclohexenylallylthiobarbituric acid and their salts. Thiopental is 5-ethyldihydro-5-(1-methylbutyl)-2-thioxo-4,6(1H,5H)-pyrimidinedione, i.e. one =O moiety in the barbituric acid structure has been replaced by =S.

Yet another group of preferred drugs for use in the present invention consists of the hydantoins. Hydantoins are, like barbituric acids, cyclic urea derivatives. The ring-opened acyl derivatives of hydantoins and barbituric acids are sometimes called ureides. Both hydantoins and barbituric acids can form urea upon hydrolysis. Hydantoins contain a 2,4-imidazolidinedione ring in their structure, a 5-membered ring with nitrogen in positions 1 and 3. The chemical name of, for example, phenytoin, is 5,5-diphenyl-2,4-imidazolidinedione. Hydantoins are closely related to barbituric acids and are acids like them.

Still another group of preferred drugs for use in the present invention consists of pyrazole derivatives. The expression "pyrazole derivatives" as used herein includes drugs containing a pyrazole ring, 3-pyrazoline ring or pyrazolidine ring in their structure, all of which are 5-membered rings with nitrogens in positions 1 and 2. These compounds are either basic or acidic. Preferred pyrazole derivatives for use herein include phenazone, phenylphenazone, metamidazole, phenylbutazone, oxyphenbutazone and sulfinpyrazone.

Yet another group of drugs preferred for use herein consists of imidazole derivatives. The expression "imidazole derivatives" as used herein includes drugs containing an imidazole, imidazoline or imidazolidine ring in their structure. These are 5-membered rings with nitrogen atoms in positions 1 and 3. These compounds are either basic or acidic. Preferred compounds of this type include histamine, miconazole, pilocarpine, naphazoline and clonidine.

Another group of preferred drugs for use in this invention are pyrimidine derivatives. These drugs contain a 6-membered ring with nitrogen atoms in positions 1 and 3. These derivatives are usually basic. Preferred pyrimidine derivatives include thiamine, trimethoprim, orotic acid, methylthiouracyl and prothiouracyl.

Still another group of preferred drugs for use herein are purine derivatives, which contain purine, that is, imidazo(4,5-d)pyrimidine, in their structures. These drugs are frequently basic but some of them are acidic. Preferred purine derivatives include caffeine, theophylline, etophylline, proxyphylline and theobromine.

Cyclic drugs having heterocyclic rings characterized as enamines, lactones, lactams, thiolactams, anhydrides, imides, imines, hemiacetals and hemiketals are thus appropriate for use in preferred embodiments of the invention, in which ring opening of the heterocyclic ring takes place.

In various aspects of the present invention, the drug is subjected to chemically reversible ring-opening so that at least a portion thereof is in ring-opened form. The portion in ring-opened form is at least 0.1% by weight, preferably at least 1 or 2% by weight, more preferably at least 5% by weight of said drug. In aqueous formulations, the amount of drug in ring-opened form is frequently from about 5 to about 10% by weight and usually no more than about 50%. In solid formulations, the portion of drug in ring-opened form can generally be much higher, frequently about 50% or more, and sometimes even about 90 to 95%.

When the method of the invention comprises complexing the drug with cyclodextrin in an aqueous medium under conditions which effect chemically reversible ring-opening of at least a portion (at least 0.1% by weight) of the drug, the complexation is advantageously conducted at a pH level which affords ring-opening of at least 5% by weight of said drug. Preferably the complexation is conducted at a pH level of below about 5.

In one preferred embodiment, the drug is a basic drug, especially a benzodiazepine, and the complexation is conducted at a pH level of below about 5. It is also preferred that the cyclodextrin is hydroxypropyl-β-cyclodextrin, β-cyclodextrin sulfobutyl ether, a branched β-cyclodextrin (especially glucosyl β-cyclodextrin or maltosyl-β-cyclodextrin), β-cyclodextrin, hydroxypropyl-γ-cyclodextrin or γ-cyclodextrin. It is also preferred that the benzodiazepine is alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam or loprazolam; and that the cyclodextrin-drug complex thus obtained be formulated as a nasal spray, sublingual tablet or parenteral solution, especially when formulated suitable for use in producing a sedative, anti-anxiety, anticonvulsant or muscle relaxant effect, most especially as a pre-anaesthetic medication, or to supplement anaesthesia, to induce and/or maintain anaesthesia or to induce a hypnotic effect. In especially preferred embodiments, the benzodiazepine is midazolam, alprazolam, clonazepam, lorazepam or triazolam; the cyclodextrin is hydroxypropyl-β-cyclodextrin, β-cyclodextrin sulfobutyl ether, a branched β-cyclodextrin (especially glucosyl β-cyclodextrin or maltosyl β-cyclodextrin), β-cyclodextrin, hydroxypropyl-γ-cyclodextrin or γ-cyclodextrin; and the complexation is conducted at a pH level below about 5, preferably between about 3 and about 5.

In another embodiment of the present method utilizing chemically reversible ring-opening described above, the drug is an acidic drug.

In yet another embodiment of the present method utilizing chemically reversible ring-opening described above, the drug is a barbituric acid derivative, a hydantoin, a pyrazole derivative, an imidazole derivative, a pyrimidine derivative or a purine derivative. When the drug is a barbituric acid derivative, it is preferably barbital, butobarbital, amobarbital, phenobarbital, aprobarbital, secobarbital, crotylbarbital, cyclobarbital, phenobarbital, hexobarbital, methylphenobarbital, thiopental, isopropylbromallylbarbituric acid, or cyclohexenylallylthiobarituric acid, or a salt thereof. When the drug is a hydantoin, it is preferably phenytoin. When the drug is a pyrazole derivative, it is preferably phenazone, propylphenazone, metamidazole, phenylbutazone, oxyphenbutazone or sulfinpyrazone. When the drug is an imidazole derivative, it is preferably histamine, miconazole, pilocarpine, naphazoline or clonidine. When the drug is a pyrimidine derivative, it is preferably thiamine, trimethoprim, orotic acid, methylthiouracyl or prothiouracyl. When the drug is a purine derivative, it is preferably caffeine, theophylline, etophylline, proxyphylline or theobromine.

When the present invention comprises complexing the drug with cyclodextrin in an aqueous medium under conditions which effect chemically reversible ring-opening of at least a portion (at least 0.1% by weight) of the drug to enhance the complexation efficacy, followed by administering the cyclodextrin-drug complex thus obtained to said animal under conditions which reduce the complexation efficacy, the complexation is generally conducted at a pH level which affords ring-opening of at least 5% by weight of the drug. Preferably, the complexation is conducted at a pH level of below about 5, especially between about 3 and about 5. The cyclodextrin is preferably hydroxypropyl-β-cyclodextrin, β-cyclodextrin sulfobutyl ether, a branched β-cyclodextrin (especially glucosyl-β-cyclodextrin or maltosyl-β-cyclodextrin), β-cyclodextrin, hydroxypropyl-γ-cyclodextrin or γ-cyclodextrin. The drug is preferably a benzodiazepine, especially midazolam, alprazolam, clonazepam, lorazepam or triazolam. The cyclodextrin-drug complex is preferably administered in the form of an aqueous solution or a hydrogel, particularly as a nasal spray or nasal drops, or as a parenteral solution. As a nasal spray of a benzodiazepine, the aqueous solution is advantageously brought to a pH level of below about 6, preferably below about 4.7, most especially to a pH between about 3 and about 4.7. When administered as a solid, the cyclodextrin-drug complex is preferably formulated as a tablet for oral, buccal or sublingual administration. The water may be removed from the aqueous complexation medium after formation of the cyclodextrin-drug complex.

When the present invention comprises subjecting a basic drug to complexation in an aqueous medium at a pH level below the pKa+2 value of said basic drug to enhance the complexation efficiency, followed by administering the cyclodextrin-drug complex thus obtained to an animal under conditions which reduce the complexation efficiency, the basic drug is preferably a benzodiazepine. Benzodiazepines of particular interest are alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam and loprazolam. Particularly preferred benzodiazepines are alprazolam, midazolam, clonazepam, lorazepam and triazolam. The cyclodextrin-benzodiazepine complex obtained in the complexation step is preferably formulated as a nasal spray, sublingual tablet or parenteral solution, which is preferably administered in an effective sedative, anti-anxiety, anticonvulsant or muscle relaxant amount, particularly as a pre-anaesthetic medication, or to supplement anaesthesia, to induce and/or maintain anaesthesia or to induce a hypnotic effect. In this general aspect of the invention, the pH level of the aqueous complexation medium is advantageously selected so that it also affords ring-opening of at least 5% by weight of the drug. For the benzodiazepines, the complexation is preferably conducted at a pH level of below about 5, most preferably between about 3 and about 5. Also in this general aspect of the invention, in one preferred embodiment, the complexation is carried out in the presence of from about 0.001 to about 5% (weight/volume) of a pharmacologically inactive, pharmaceutically acceptable water-soluble polymer at a temperature of from about 30° C. to about 150° C. Preferably, the polymer is a cellulose derivative or a polyvinyl polymer; more preferably, the polymer is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose, sodium carboxymethylcellulose or polyvinylpyrrolidone. An especially preferred cellulose derivative is hydroxypropyl methylcellulose. A method for enhancing drug-cyclodextrin complexation utilizing a pharmacologically inactive water-soluble polymer is described in Loftsson U.S. Pats. No. 5,324,718 and No. 5,472,954, both of which are incorporated by reference herein in their entireties and relied upon. In another preferred embodiment of this general aspect of the invention, the complexation is also carried out in the presence of acetic acid and/or one or more pharmaceutically acceptable salts of acetic acid, the acetate-water ratio of the aqueous complexation medium being from about 1:1000 to about 2:1, preferably from about 1:100 to about 1:1, more preferably from about 1:20 to about 1:4. Preferably, the drug is midazolam and the cyclodextrin is hydroxypropyl-β-cyclodextrin, β-cyclodextrin sulfobutyl ether, a branched β-cyclodextrin (especially glucosyl-β-cyclodextrin or maltosyl-β-cyclodextrin), β-cyclodextrin, hydroxypropyl-γ-cyclodextrin or γ-cyclodextrin.

When the present invention comprises subjecting an acidic drug to complexation in an aqueous medium at a pH level above the pKa-2 value of said acidic drug to enhance the complexation efficiency, followed by administering the cyclodextrin-drug complex thus obtained to an animal under conditions which reduce the complexation efficiency, preferably the pH level of the aqueous complexation medium is selected such that it also affords ring-opening of at least 5% by weight of said drug.

In order to further illustrate the present invention and the advantages thereof, the following specific examples are given, it being understood that same are intended only as illustrative and in no way limitative of the invention.

EXAMPLE 1

Phenytoin (5,5-diphenylhydantoin) is a water-insoluble weak acid (pKa 8.1) which forms a somewhat water-soluble anion in alkaline solution. Solubility (S) of phenytoin at three different pH levels was determined in aqueous solutions containing various amounts of 2-hydroxypropyl-β-cyclodextrin (HPβCD) of molar substitution (MS)=0.9, i.e. (a) pH 2.74±0.18 (SD), (b) pH 7.55±0.12, and (c) pH 10.19±0.14. Excess amount of the drug was added to the aqueous HPβCD solution and the suspension formed sonicated for one hour at room temperature (23° C.). After equilibration at 25° C. in a water-bath for three days, the suspension was filtered through a 0.45 μm membrane filter, diluted with aqueous methanolic solution and the amount of dissolved phenytoin determined by a high pressure liquid chromatographic method (HPLC). FIG. 1 illustrates the effect of pH on the phase-solubility of phenytoin (pKa 8.1) in aqueous HPβCD solutions at 25° C. The results set forth in FIG. 1 show significant enhancement in the HPβCD solubilization (i.e. the efficiency of the complexation) of the drug at pH 10.19 (♦) where the drug is mainly in the ionized form. Formation of phenytoin-HPβCD complexes at pH 10.19 can result in enhanced bioavailability of phenytoin. For example, topical application of such a solution to the skin will result in lowering of pH, which will decrease the efficiency of the complexation, which again will result in enhanced permeability of phenytoin into and through the skin. Also, formation of phenytoin-HPβCD complexes at pH of about 10 (e.g. in aqueous ammonia solutions) and lyophilization of the complex will result in phenytoin-HPβCD complex powder which can, for example, be formulated into tablets. The bioavailability of phenytoin from such tablets will be enhanced compared to the phenytoin availability from tablets containing phenytoin-HPβCD complex prepared at lower pH, e.g. at pH 2.7 (●) or 7.6 (■).

EXAMPLE 2

Figure 2:
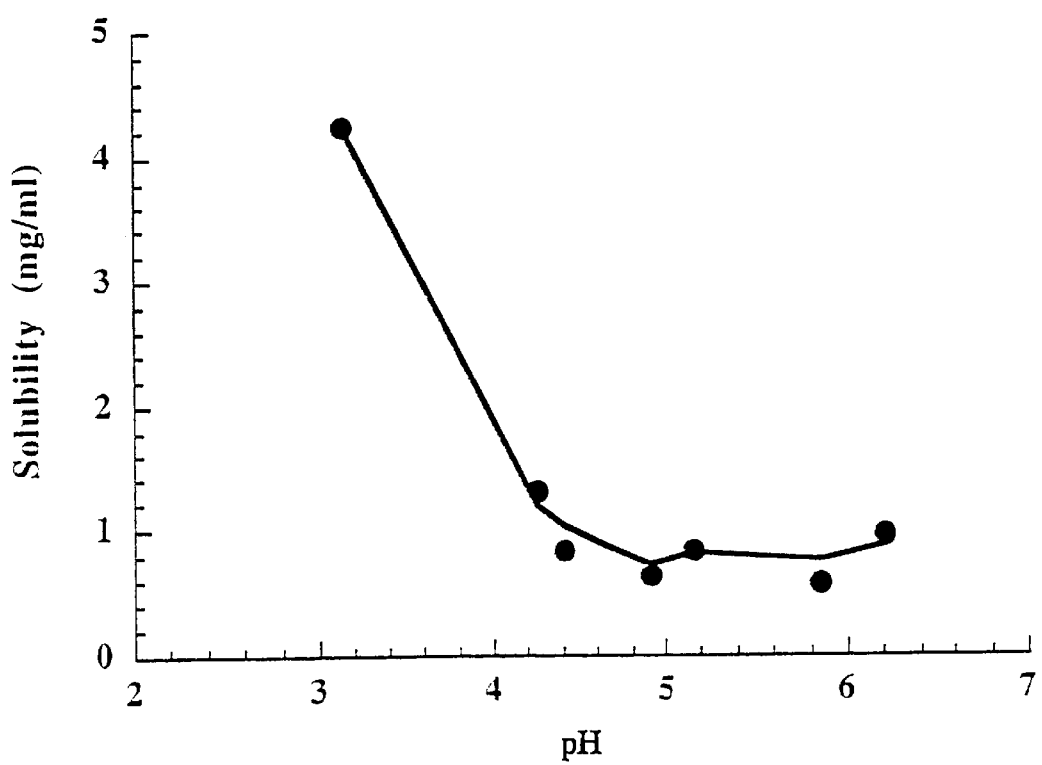
FIG. 2 is a graph illustrating the effect of pH on the solubility of alprazolam (pKa 2.4) in aqueous 10% (w/v) HPβCD solutions at room temperature.

Alprazolam is a water-insoluble weak base (pKa 2.41) which forms a somewhat water-soluble cation in acidic solution. Solubility (S) of alprazolam at several different pH levels was determined in aqueous solutions containing 10% (w/v) 2-hydroxypropyl-β-cyclodextrin (HPβCD) of molar substitution (MS)=0.3. Excess amount of the drug was added to the aqueous HPβCD solution and the suspension formed heated in a sealed container in an autoclave (120–140° C. for 20–40 minutes). After equilibration at room temperature (22–23° C.) for seven days, the suspension was filtered through a 0.45 μm membrane filter, diluted with aqueous methanolic solution and the amount of dissolved alprazolam determined by a high pressure liquid chromatographic method (HPLC). FIG. 2 illustrates the effect of pH on the solubility of alprazolam (pKa 2.4) in aqueous 10% (w/v) HPβCD solutions at room temperature. The results set forth in FIG. 2 show significant enhancement in the HPβCD solubilization (i.e. the efficiency of the complexation) of the drug at a pH at which the drug is mainly in the ionized form. The sharp increase in the solubility can, however, only partly be explained by the ionization of the alprazolam molecule.

EXAMPLE 3

Several drugs which have a nitrogen-containing heterocycle in their structure are known to undergo reversible ring-opening which frequently is pH dependent. For example, barbituric acids undergo reversible ring cleavage (H. J. Roth, K. Eger and R. Troschütz, *Pharmaceutical Chemistry. Volume 2. Drug Analysis.* Ellis Horwood, 1991, pp. 308–309):

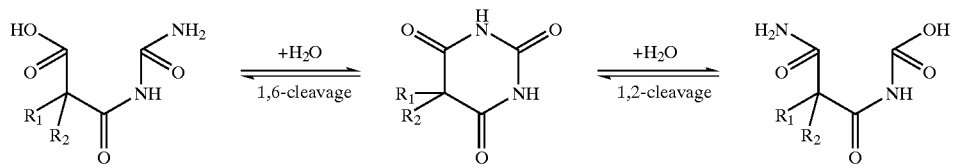

Another example of such reversible ring-opening is the opening of cyclic imines through formation of an aldehyde or ketone and a primary amine:

Another example of such reversible ring-opening is the opening of cyclic imines through formation of an aldehyde or ketone and a primary amine:

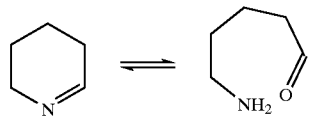

An example of such structure is the 1H-1,4-diazepine ring which, for example, is an essential structure of the benzodiazepine derivatives. These structural changes are pH-dependent and reversible, and it is known that the open form frequently co-exists with the closed one in several commercial products. One example is the iv solution of midazolam (Dormicum™ from F. Hoffmann-LaRoche & Ltd, Switzerland) where the drug is partly in the open form (M. Gerecke, "Chemical structure and properties of midazolam compared with other benzodiazepines", *Br. J. Clin. Pharmac.*, 11S–16S (1983)). However, the open form of midazolam is rapidly converted to the closed one upon iv administration.

We have determined the effect of pH and cyclodextrins, i.e. HPβCD MS 0.3, sulfobutylether β-cyclodextrin (SBEβCD) with degree of substitution (DS)=6.4, α-cyclodextrin (αCD) and γ-cyclodextrin (γCD) on the ring-opening of several benzodiazepines. The cyclodextrin concentration was 10% (w/v) and the benzodiazepine concentration was $1 \times 10^{-4}$ M. The concentration of the closed form was determined immediately after dissolving the benzodiazepine in the aqueous cyclodextrin solution and again 24 hours later (i.e. after equilibration at 23° C.). Preliminary experiments had shown that equilibrium between the closed and the open form was attained within 3 hours at 23° C.

It is clear from the results displayed in Table 3 below that a large fraction of the benzodiazepines (over 50% at pH below 2) are in the open form at low pH and that the fraction of open form frequently increases upon addition of cyclodextrin to the aqueous solution. For example, at pH 3 about 60% of alprazolam in aqueous HPβCD solution is in the open form. This will increase the apparent intrinsic solubility ($S_0$). This increase in $S_0$ will result in enhanced complexation efficiency. The observed increase in the complexation efficiency will result in enhanced cyclodextrin solubilization of the benzodiazepines in aqueous solutions.

TABLE 3

The effect of pH and cyclodextrins on the fraction of the open form of several benzodiazepines at room temperature (approx. 23° C.).

| Benzodiazepine | Cyclodextrin | pH | Fraction open |
|---|---|---|---|
| Alprazolam (pKa 2.4) | None | 2 | 0.82 |
| | | 3 | 0.56 |
| | | 4 | 0.33 |
| | HPβCD | 2 | 0.89 |
| | | 3 | 0.60 |
| | | 4 | 0.23 |
| | SBEβCD | 2 | 0.96 |
| | | 3 | 0.84 |
| | | 4 | 0.33 |
| | αCD | 2 | 0.94 |
| | | 3 | 0.79 |
| | | 4 | 0.25 |
| | γCD | 2 | 0.81 |
| | | 3 | 0.41 |
| | | 4 | 0.42 |
| Diazepam (pKa 3.3) | None | 2 | 0.30 |
| | | 3 | 0.23 |
| | | 4 | 0.15 |

TABLE 3-continued

The effect of pH and cyclodextrins on the fraction of the open form of several benzodiazepines at room temperature (approx. 23° C.).

| Benzodiazepine | Cyclodextrin | pH | Fraction open |
|---|---|---|---|
| | HPβCD | 2 | 0.65 |
| | | 3 | 0.29 |
| | | 4 | 0.15 |
| | SBEβCD | 2 | 0.63 |
| | | 3 | 0.56 |
| | | 4 | 0.22 |
| | αCD | 2 | 0.67 |
| | | 3 | 0.51 |
| | | 4 | 0.13 |
| | γCD | 2 | 0.41 |
| | | 3 | 0.17 |
| | | 4 | 0.13 |
| Midazolam (pKa 6.2) | None | 2 | 0.74 |
| | | 3 | 0.28 |
| | | 4 | 0.18 |
| | HPβCD | 2 | 0.56 |
| | | 3 | 0.18 |
| | | 4 | 0.23 |
| | SBEβCD | 2 | 0.81 |
| | | 3 | 0.39 |
| | | 4 | 0.11 |
| | αCD | 2 | 0.79 |
| | | 3 | 0.32 |
| | | 4 | 0.10 |
| | γCD | 2 | 0.61 |
| | | 3 | 0.21 |
| | | 4 | 0.17 |
| Triazolam (pKa between 2 and 3) | None | 2 | 0.53 |
| | | 3 | 0.08 |
| | | 4 | 0.00 |
| | HPβCD | 2 | 0.51 |
| | | 3 | 0.09 |
| | | 4 | 0.00 |
| | SBEβCD | 2 | 0.71 |
| | | 3 | 0.25 |
| | | 4 | 0.00 |
| | αCD | 2 | 0.75 |
| | | 3 | 0.23 |
| | | 4 | 0.00 |
| | γCD | 2 | 0.33 |
| | | 3 | 0.01 |
| | | 4 | 0.00 |

EXAMPLE 4

Figure 3:
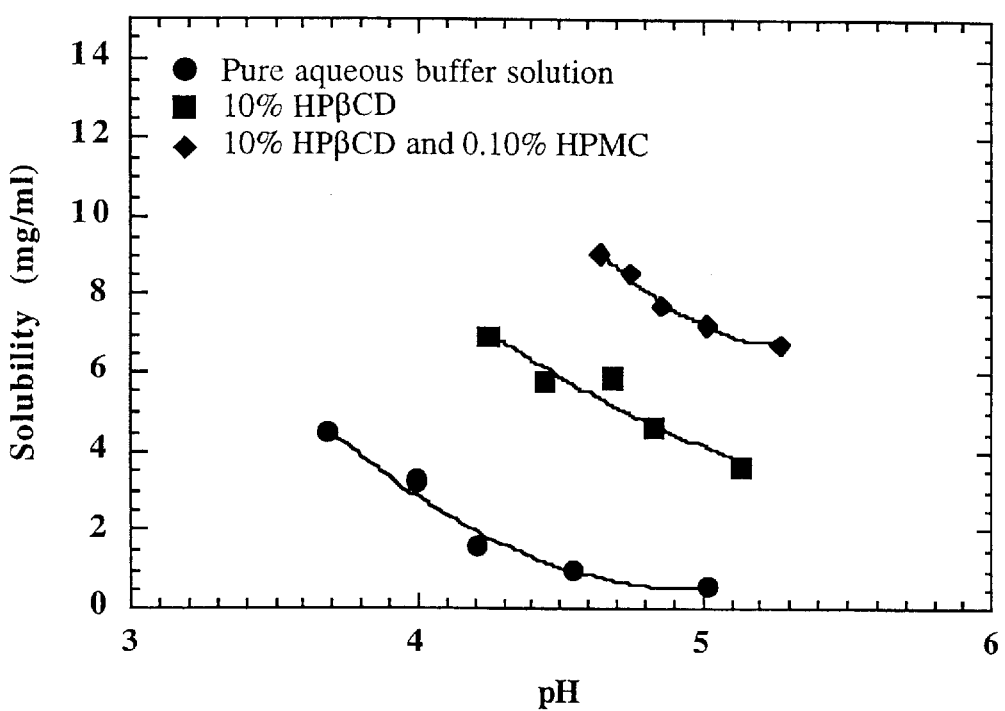
FIG. 3 is a graph illustrating the effect of pH (i.e. the diazepine ring-opening) on the solubility of midazolam (pKa 6.2) in pure aqueous buffer solutions (●), aqueous buffer solutions containing 10% (w/v) HPβCD (■) and aqueous buffer solutions containing both 10% (w/v) HPβCD and 0.10% (w/v) hydroxypropyl methylcellulose (HPMC) (♦) at room temperature.

Midazolam is a water-insoluble weak base (pKa 6.2) which forms a somewhat water-soluble cation in acidic solution. Solubility (S) of midazolam at several different pH levels was determined in: a) pure aqueous buffer solutions (i.e. without HPβCD and HPMC); b) aqueous buffer solutions containing 10% (w/v) 2-hydroxypropyl-β-cyclodextrin (HPβCD) of molar substitution (MS)=0.3; and c) aqueous solutions containing 10% (w/v) 2-hydroxypropyl-β-cyclodextrin (HPβCD) of molar substitution (MS)=0.3 and 0.10% (w/v) hydroxypropyl methylcellulose (HPMC) 4000. Excess amount of the drug was added to the aqueous solution and the suspension formed was heated in a sealed container in an autoclave (120–140° C. for 20–40 minutes). After equilibration at room temperature (22–23° C.) for seven days, the suspension was filtered through a 0.45 μm membrane filter, diluted with aqueous methanolic solution and the amount of dissolved midazolam determined by a high pressure liquid chromatographic method (HPLC). FIG. 3 illustrates the effect of pH (i.e. the ring-opening) on the solubility of midazolam (pKa 6.2) in pure aqueous buffer solutions (●), aqueous buffer solutions containing 10% (w/v) HPβCD (■), and aqueous buffer solutions containing both 10% (w/v) HPβCD and 0.10% (w/v) HPMC (♦) at room temperature. The results set forth in FIG. 3 show significant enhancement in the HPβCD solubilization (i.e. the efficiency of the complexation) of the drug at pH levels where the drug exists partly in the open form. Addition of HPMC significantly improves the efficiency.

EXAMPLE 5

Figure 4:
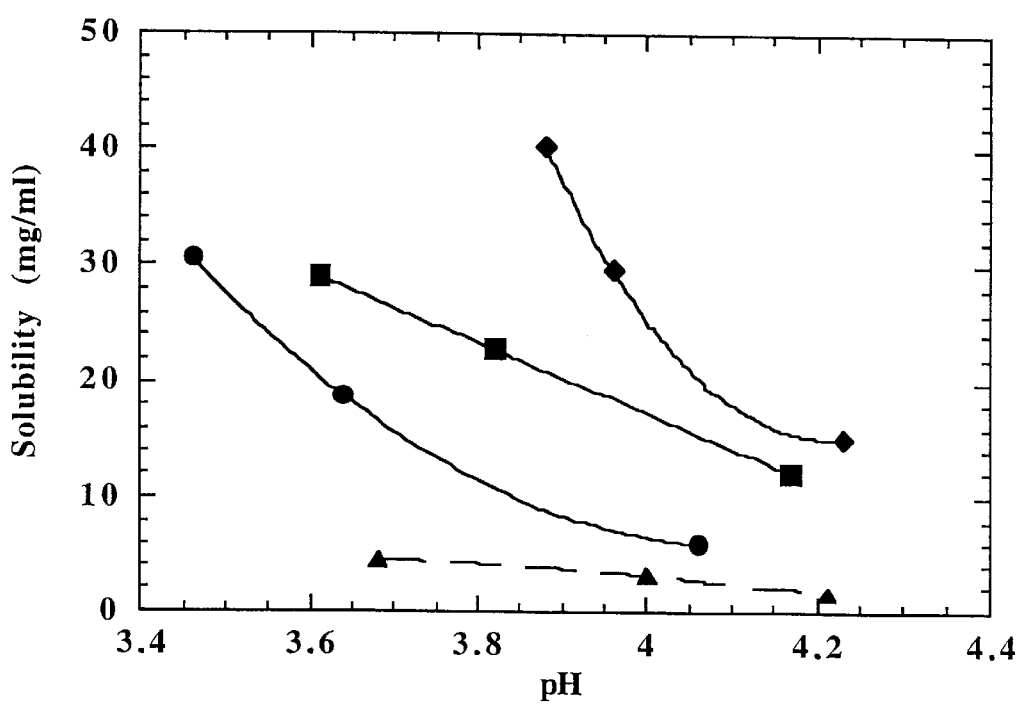
FIG. 4 is a graph illustrating the effects of cyclodextrins, pH and 10% (v/v) acetic acid on the solubility of midazolam in aqueous solutions: pure aqueous buffer solution (♦); aqueous 10% (v/v) acetic acid solution (●); 10% w/v HPβCD solution containing 0.10% (w/v) HPMC in aqueous 10% (v/v) acetic acid solution (■); 10% (w/v) aqueous sulfobutyl ether-β-cyclodextrin (SBEβCD) solution in aqueous 10% (v/v) acetic acid solution (♦)

Solubility (S) of midazolam at several different pH levels was determined in: a) pure aqueous buffer solutions (i.e. without cyclodextrin, polymer or acetic acid); b) aqueous buffer solutions containing 10% (v/v) acetic acid as a co-solvent; c) aqueous buffer solutions containing 10% (w/v) sulfobutylether β-cyclodextrin (SBEβCD) and 10% (v/v) acetic acid as a co-solvent; and d) aqueous buffer solutions containing 10% (w/v) 2-hydroxypropyl-β-cyclodextrin (HPβCD), 0.10% (w/v) hydroxypropyl methylcellulose (HPMC) and 10% (v/v) acetic acid as a co-solvent. Excess amount of the drug was added to the aqueous HPβCD solution and the suspension formed was heated in a sealed container in an autoclave (120–140° C. for 20–40 minutes). After equilibration at room temperature (22–23° C.) for seven days, the suspension was filtered through a 0.45 μm membrane filter, diluted with aqueous methanolic solution and the amount of dissolved midazolam determined by a high pressure liquid chromatographic method (HPLC). FIG. 4 illustrates the effects of cyclodextrins, pH and 10% (v/v) acetic acid on the solubility of midazolam in aqueous solutions: pure aqueous buffer solution (▲); aqueous 10% (v/v) acetate solution (●); 10% (w/v) HPβCD solution containing 0.10% (w/v) HPMC in aqueous 10% (v/v) acetic acid solution (■); 10% (w/v) aqueous SBEβCD solution in aqueous 10% (v/v) acetate (♦). The results set forth in FIG. 4 show that addition of 10% (v/v) acetic acid significantly improves the complexation. Addition of the acetic acid increases the value of $S_0$ without having any significant effect on the value of $K_C$, which significantly improves the complexation efficiency and, consequently, enhances the cyclodextrin solubilization of the drug. Midazolam carries a positive charge at acidic pH and, thus, the negatively charged SBEβCD forms a more stable complex than the uncharged HPβCD with midazolam at these conditions. Addition of 10% (v/v) acetic acid as a co-solvent resulted in a small decrease in the fraction of the open ring form of the drug.

EXAMPLE 6

Female hairless mice were sacrificed by cervical dislocation and their full-thickness skins removed. The outer surface of the skin was rinsed with 35% (v/v) methanol in water and subsequently with distilled water to remove any contamination. The skin was placed in Franz diffusion cells. The receptor phase consisted of phosphate buffer saline pH 7.4. The skin diffusion cells were stirred with a magnetic bar and kept at 37° C. by circulating water through an external jacket. The donor phase (2.0 ml) consisted of a solution of the drug in aqueous 7% (w/v) SBEβCD solution pH 3.3, or aqueous cyclodextrin solution where the pH had been raised from 3.3 to 4.1 (by addition of NaOH) before it was applied to the skin. The alprazolam concentration in the donor phase was 1.85 mg/ml at pH 3.3. Samples (200 μl) of receptor phase were removed from the cells at various time intervals up to 48 hours and replaced with a fresh buffer solution. The samples were kept frozen until analyzed by HPLC. The flux was calculated from the linear part of each permeability profile and the permeability coefficient obtained by dividing the flux with the concentration of dissolved drug in the donor phase. The results set forth in Table 4 show clearly that raising the pH from 3.3 to 4.1 increases the flux though biological membranes such as hairless mouse skin.

TABLE 4

The flux of alprazolam through hairless mouse skin.
The donor phase consisted of aqueous pH 3.3 buffer solution containing 7% (w/v) SBEβCD saturated with the drug.
In one case the pH of the donor phase was kept constant at pH 3.3, but in the other case the pH was raised to 4.1 (by addition of NaOH) before it was applied to the skin.
The alprazolam concentration in the donor phase was 1.85 mg/ml at pH 3.3.

| Donor phase | Flux (mg/cm$^2$/h) | Ratio |
|---|---|---|
| Without increasing the pH | $3.91 \times 10^{-4}$ | 1.0 |
| Increasing the pH from 3.3 to 4.1 | $4.56 \times 10^{-4}$ | 1.2 |

EXAMPLE 7

The effect of cyclodextrins and organic solvents on the rate of diazepine ring-closure of several selected benzodiazepines was investigated. Stock solutions containing $1.0 \times 10^{-3}$ M of the benzodiazepine in 0.10 M aqueous hydrochloric acid solution (pH approx. 1.1) were prepared and stored at 37.0° C. The benzodiazepines were in the ring-open form in these stock solutions. Aqueous 0.50 M tris buffer (pH 7.50) solution was prepared. The observed first-order rate constant for the closing (i.e. formation) of the benzodiazepine ring was determined in the following reaction media: a) pure aqueous tris buffer solution; b) aqueous tris buffer solution containing 10% (w/v) cyclodextrin; c) tris buffer solution containing 10% (w/v) cyclodextrin and 10% (v/v) ethanol (EtOH); d) tris buffer solution containing 10% (w/v) cyclodextrin and 50% (v/v) EtOH; e) tris buffer solution containing 10% (w/v) cyclodextrin and 10% (v/v) dimethylsulfoxide (DMSO); and f) tris buffer solution containing 10% (w/v) cyclodextrin and 50% (w/v) DMSO. The stock solution (30 μl) was added to 1.50 ml of the reaction media which had previously been equilibrated to 37.0° C. and the first-order rate constant for the appearance of the closed form determined from the appearance of the closed form as observed on HPLC. Tables 5, 6 and 7 show the effects of cyclodextrins, EtOH and DMSO on the observed first-order rate constant for the regeneration of alprazolam, triazolam and midazolam, respectively. In pure aqueous buffer solutions, addition of EtOH and DMSO decreases somewhat the rate of ring closure, at least in the case of alprazolam and midazolam. Addition of cyclodextrin or the organic solvents have insignificant effect on the pH under these conditions. The dielectric constant of the reaction medium will, however, decrease upon addition of the organic solvents. It is possible that this decrease in the dielectric constant will reduce the ability of the reaction media to stabilize the transition state which could explain the decrease in the observed rate constant. Addition of cyclodextrin decreased significantly, in all cases, the rate of ring closure. The cyclodextrins formed stable complexes with the ring-open form of the drug and, thus, the rate decreased upon addition of cyclodextrin. Addition of EtOH or DMSO to the cyclodextrin-containing reaction media resulted in increase in the rate, compared to reaction media containing only cyclodextrin, which could be due to decreased complexation of the diazepine ring-open form. EtOH and DMSO will compete with the diazepine ring-open form for a space in the cyclodextrin cavity resulting in decreased complexation.

TABLE 5

The effect of cyclodextrins, ethanol (EtOH) and dimethylsulfoxide (DMSO) on the first-order rate constant for the formation of the diazepine ring, i.e. regeneration of alprazolam, at pH 7.5 and 37° C.

| | The observed first-order rate constant × 10$^2$ (min$^{-1}$) | | | | |
|---|---|---|---|---|---|
| Cyclodextrin | Pure water | 10% EtOH | 50% EtOH | 10% DMSO | 50% DMSO |
| No CD | 14.2 | 11.5 | 7.24 | 9.68 | 10.7 |
| 10% RMβCD | 2.97 | 4.90 | 6.70 | 3.97 | 7.92 |
| 10% HPβCD | 3.30 | 5.23 | 7.07 | 4.44 | 8.57 |
| 10% SBEβCD | 3.11 | 5.18 | 5.82 | 4.77 | 9.36 |

TABLE 6

The effect of cyclodextrins, ethanol (EtOH) and dimethylsulfoxide (DMSO) on the first-order rate constant for the formation of the diazepine ring, i.e. regeneration of triazolam, at pH 7.5 and 37° C.

| | The observed first-order rate constant × 10$^{-2}$ (min$^{-1}$) | | | | |
|---|---|---|---|---|---|
| Cyclodextrin | Pure water | 10% EtOH | 50% EtOH | 10% DMSO | 50% DMSO |
| No CD | 1.32 | 1.31 | 1.84 | 1.28 | 1.37 |
| 10% RMβCD | 0.64 | 0.92 | 1.00 | 0.78 | 1.12 |
| 10% HPβCD | 0.66 | 0.92 | 1.02 | 0.79 | 1.14 |
| 10% SBEβCD | 0.58 | 0.82 | 0.97 | 0.73 | 1.13 |

TABLE 7

The effect of cyclodextrins, ethanol (EtOH) and dimethylsulfoxide (DMSO) on the first-order rate constant for the formation of the diazepine ring, i.e. regeneration of midazolam, at pH 7.5 and 37° C.

| | The observed first-order rate constant × 10$^{-2}$ (min$^{-1}$) | | | | |
|---|---|---|---|---|---|
| Cyclodextrin | Pure water | 10% EtOH | 50% EtOH | 10% DMSO | 50% DMSO |
| No CD | 17.9 | 12.6 | 8.41 | 13.8 | 10.9 |
| 10% RMβCD | 3.05 | 4.24 | 6.99 | 4.94 | 8.48 |
| 10% HPβCD | 2.77 | 3.86 | 6.53 | 3.36 | 8.40 |
| 10% SBEβCD | 1.30 | 3.30 | 6.50 | 2.24 | 8.55 |

EXAMPLE 8

Figure 5:
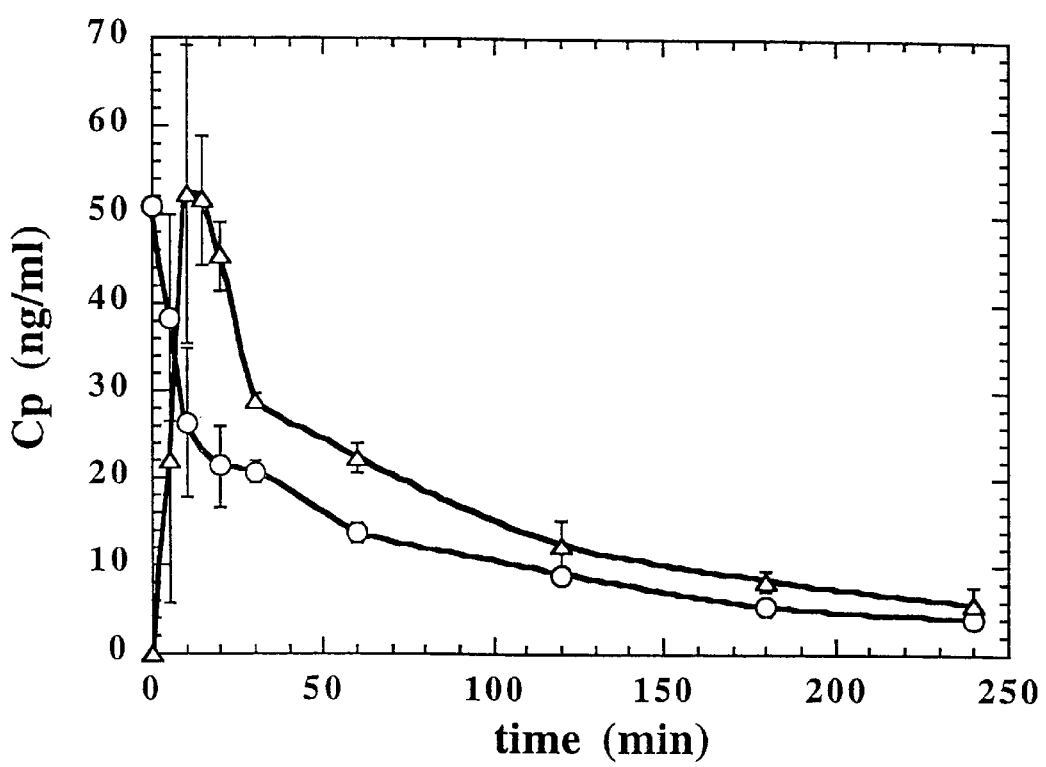
FIG. 5 is a graph plotting the concentration in ng/ml of midazolam in serum after intravenous administration of 2 mg of a commercial intravenous formulation of midazolam (○) and nasal administration of 4.8 mg of a nasal formulation of midazolam prepared in accord with the present invention (Δ), against time in minutes, where each point represents the mean value and error bars represent standard deviation.

The bioavailability of midazolam in a nasal spray according to the invention was evaluated. The composition of the midazolam nasal spray was as follows: midazolam 1.70% (w/v), sulfobutylether β-cyclodextrin sodium salt (Captisol®) 14.00% (w/v), benzalkonium chloride 0.02% (w/v), sodium edetate (EDTA tetrasodium) 0.10% (w/v), hydroxypropyl methylcellulose 0.10% (w/v), phosphoric acid 0.50% (v/v), sodium hydroxide quantum satis ad pH 4.35 in purified water. The intravenous (iv) dose was fixed at 2 mg (Dormicum™ 5 mg/ml iv solution from F. Hoffmann-La Roche & Ltd., Switzerland) but the intranasal (in) dose was 0.06 mg/kg or 4.84 mg (285 μl nasal spray) on the average. This was a cross-over study where each individual received both the iv and in formulation (via nasal spray) with a one week resting period between administrations. Serum samples were collected at various time points after administration of the drug and the midazolam concentration determined with an HPLC method. FIG. 5 illustrates the concentration profile of midazolam in serum after administration of 2 mg of midazolam intravenously (○) or 4.8 mg of midazolam intranasally (Δ). Each point represents the mean value; error bars represent standard deviation. The bioavailability of midazolam after intranasal administration was determined to be 61% and the mean $C_p^{max}$ was determined to be 52 ng/ml at 12 min after intranasal administration of the drug. Sedation was not observed after the iv administration but sedation was observed in all three individuals within 10 min after intranasal administration of the drug. This sedation lasted for about one and one-half hours. Insignificant irritation was observed in the three individuals tested after intranasal administration of the drug.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A method for enhancing the complexation efficiency of a benzodiazepine with a cyclodextrin, said method comprising complexing said benzodiazepine with β-cyclodextrin sulfobutyl ether in an aqueous medium at a pH level below about 5 and allowing the resultant complexation medium to equilibrate for sufficient time to effect enhanced solubilization of said benzodiazepine.

2. A method according to claim 1, wherein the benzodiazepine is alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam or loprazolam.

3. A method according to claim 2, further comprising formulating the cyclodextrin-benzodiazepine complex thus obtained as a nasal spray, sublingual tablet or parenteral solution.

4. A method according to claim 3, wherein the benzodiazepine is alprazolam, clonazepam, lorazepam, midazolam or triazolam.

5. A method according to claim 1, wherein the complexation is conducted at a pH level between about 3 and about 5.

6. A method for enhancing the availability of a benzodiazepine following administration of a cyclodextrin-benzodiazepine complex to a warm-blooded animal in need of same, said method comprising complexing said benzodiazepine with β-cyclodextrin sulfobutyl ether in an aqueous medium at a pH level below about 5 and allowing the resultant complexation medium to equilibrate for sufficient time to effect enhanced solubilization of said benzodiazepine, further comprising administering the cyclodextrin-benzodiazepine complex thus obtained to said animal.

7. A method according to claim 6, wherein the benzodiazepine is alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam or loprazolam.

8. A method according to claim 7, further comprising formulating the cyclodextrin-benzodiazepine complex thus obtained as a nasal spray, sublingual tablet or parenteral solution.

9. A method according to claim 8, further comprising administering the nasal spray, sublingual tablet or parenteral solution in a quantity sufficient to produce a sedative, anti-anxiety, anticonvulsant or muscle relaxant effect.

10. A method according to claim 9, further comprising administering the nasal spray, sublingual tablet or parenteral solution as a pre-anaesthetic medication, or to supplement anaesthesia, to induce and maintain anaesthesia or to induce a hypnotic effect.

11. A method according to claim 10, wherein the benzodiazepine is alprazolam, clonazepam, lorazepam, midazolam or triazolam.

12. A method according claim 11, wherein the complexation is conducted at a pH level between about 3 and about 5.

13. A method according to claim 6, further comprising formulating the cyclodextrin-benzodiazepine complex thus obtained as an aqueous solution or a hydrogel.

14. A method according to claim 13, further comprising administering the cyclodextrin-benzodiazepine complex as a nasal spray or nasal drops.

15. A method according to claim 13, further comprising administering the cyclodextrin-benzodiazepine complex as a parenteral solution.

16. A method according to claim 13, wherein said benzodiazepine is selected from the group consisting of midazolam, alprazolam, clonazepam, lorazepam and triazolam and wherein the cyclodextrin-drug complex is formulated as an aqueous solution.

17. A method according to claim 16, further comprising formulating the aqueous solution to be at a pH level of below about 4.7 and administering it as a nasal spray.

18. A method according to claim 17, wherein the pH level of the nasal spray is between about 3 and about 4.7.

19. A method according to claim 6, further comprising formulating the cyclodextrin-benzodiazepine complex thus obtained for dermal administration.

20. A method according to claim 6, further comprising formulating the cyclodextrin-benzodiazepine complex thus obtained as a solid.

21. A method according to claim 20, wherein the solid cyclodextrin-benzodiazepine complex is formulated as a tablet for oral, buccal or sublingual administration.

22. A method for enhancing the availability of a benzodiazepine following administration of a cyclodextrin-benzodiazepine complex to a warm-blooded animal in need of same, said method comprising complexing said benzodiazepine with β-cyclodextrin sulfobutyl ether in an aqueous medium at a pH level below about 5 and allowing the resultant complexation medium to equilibrate for sufficient time to effect enhanced solubilization of said benzodiazepine, removing the water from the aqueous complexation medium after formation of the cyclodextrin-benzodiazepine complex, and administering the cyclodextrin-benzodiazepine complex thus obtained to said animal.

23. A method according to claim 22, wherein the benzodiazepine is alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam or loprazolam.

24. A method according to claim 22, wherein the benzodiazepine is midazolam, alprazolam, clonazepam, lorazepam or triazolam.

25. A method according to claim 6, further comprising complexing said benzodiazepine with β-cyclodextrin sulfobutyl ether in the presence of from about 0.0001 to about 5% (weight/volume) of a pharmacologically inactive, pharmaceutically acceptable water-soluble polymer at a temperature of from about 30° C. to about 150° C.

26. A method according to claim 25, wherein the polymer is a cellulose derivative or a polyvinyl polymer.

27. A method according to claim 26, wherein the polymer is methylcellulose, hydroxyethyl cellulose, hydroxypropyl cellulose, hydroxypropyl methylcellulose, hydroxyethyl methylcellulose, hydroxypropyl ethylcellulose, hydroxyethyl ethylcellulose, sodium carboxymethylcellulose or polyvinylpyrrolidone.

28. A method according to claim 27, wherein the cellulose derivative is hydroxypropyl methylcellulose.

29. A method according to claim 6, further comprising complexing said benzodiazepine with β-cyclodextrin sulfobutyl ether in the presence of at least one member selected from the group consisting of acetic acid and its pharmaceutically acceptable salts, the acetate-water ratio of the aqueous complexation medium being from about 1:1000 to about 2:1.

30. A method according to claim 29, wherein the benzodiazepine is midazolam.

31. A method according to claim 6, further comprising complexing said benzodiazepine with β-cyclodextrin sulfobutyl ether in the presence of from about 0.001 to about 5% (weight/volume) of a pharmacologically inactive, pharmaceutically acceptable water soluble polymer at a temperature of from about 30° C. to about 150° C., and further in the presence of at least one member selected from the group consisting of acetic acid and its pharmaceutically acceptable salts, the acetate-water ration of the aqueous complexation medium being from about 1:1000 to about 2:1.

32. A method according to claim 31, wherein the benzodiazepine is midazolam.

33. A method for enhancing the complexation efficiency of a benzodiazepine with cyclodextrin, said method comprising complexing said benzodiazepine with a cyclodextrin selected from the group consisting of α-cyclodextrin, β-cyclodextrin, γ-cyclodextrin, methylated α-cyclodextrin, methylated β-cyclodextrin, methylated γ-cyclodextrin, hydroxypropyl-α-cyclodextrin, hydroxypropyl-β-cyclodextrin, hydroxypropyl-γ-cyclodextrin, maltosyl-α-cyclodextrin, maltosyl-β-cyclodextrin, maltosyl-γ-cyclodextrin, β-cyclodextrin sulfobutyl ether, hydroxyethyl-β-cyclodextrin, hydroxyethyl-γ-cyclodextrin, α-cyclodextrin carboxymethyl ether, β-cyclodextrin carboxymethyl ether and γ-cyclodextrin carboxymethyl ether, in an aqueous medium at a pH level below about 5 and allowing the resultant complexation medium to equilibrate for sufficient time to effect enhanced solubilization of said benzodiazepine, further comprising detecting the enhanced solubilization of said benzodiazepine.

34. A method for enhancing the complexation efficiency of a benzodiazepine with a cyclodextrin, said method comprising complexing said benzodiazepine with a cyclodextrin selected from the group consisting of a α-cyclodextrin, β-cyclodextrin, γ-cyclodextrin, methylated α-cyclodextrin, methylated β-cyclodextrin, methylated γ-cyclodextrin, hydroxypropyl-α-cyclodextrin, hydroxypropyl-β-cyclodextrin, hydroxypropyl-γ-cyclodextrin, maltosyl-α-cyclodextrin, maltosyl-β-cyclodextrin, maltosyl-γ-cyclodextrin, β-cyclodextrin sulfobutyl ether, hydroxyethyl-β-cyclodextrin, hydroxyethyl-γ-cyclodextrin, α-cyclodextrin carboxymethyl ether, β-cyclodextrin carboxymethyl ether and γ-cyclodextrin carboxymethyl ether, in an aqueous medium at a pH level below about 5 and allowing the resultant complexation medium to equilibrate for sufficient time to effect enhanced solubilization of said benzodiazepine.

35. A method for enhancing the availability of a benzodiazepine following administration of a cyclodextrin-benzodiazepine complex to a warm-blooded animal in need of same, said method comprising complexing said benzodiazepine with a cyclodextrin selected from the group consisting of α-cyclodextrin, β-cyclodextrin, γ-cyclodextrin, methylated α-cyclodextrin, methylated β-cyclodextrin, methylated γ-cyclodextrin, hydroxypropyl-α-cyclodextrin, hydroxypropyl-β-cyclodextrin, hydroxypropyl-γ-cyclodextrin, maltosyl-α-cyclodextrin, maltosyl-β-cyclodextrin, maltosyl-γ-cyclodextrin, β-cyclodextrin sulfobutyl ether, hydroxyethyl-β-cyclodextrin, hydroxyethyl-γ-cyclodextrin, α-cyclodextrin carboxymethyl ether, β-cyclodextrin carboxymethyl ether and γ-cyclodextrin carboxymethyl ether, in an aqueous medium at a pH level below about 5 and allowing the resultant complexation medium to equilibrate for sufficient time to effect enhanced solubilization of said benzodiazepine, further comprising formulating the cyclodextrin-benzodiazepine complex thus obtained into a form suitable for administration to said animal, raising the pH level with base to above the pH level for the complexation, and administering said form.

36. A method for enhancing the availability of a benzodiazepine following administration of a cyclodextrin benzodiazepine complex to a warm-blooded animal in need of same, said method comprising complexing said benzodiazepine with a cyclodextrin selected from the group consisting of α-cyclodextrin, β-cyclodextrin, γ-cyclodextrin, methylated α-cyclodextrin, methylated β-cyclodextrin, methylated γ-cyclodextrin, hydroxypropyl-α-cyclodextrin, hydroxypropyl-β-cyclodextrin, hydroxypropyl-γ-cyclodextrin, maltosyl-α-cyclodextrin, maltosyl-β-cyclodextrin, maltosyl-γ-cyclodextrin, β-cyclodextrin sulfobutyl ether, hydroxyethyl-β-cyclodextrin, hydroxyethyl-γ-cyclodextrin, α-cyclodextrin carboxymethyl ether, β-cyclodextrin carboxymethyl ether and γ-cyclodextrin carboxymethyl ether in an aqueous medium at a pH level below about 5 and allowing the resultant complexation medium to equilibrate for sufficient time to effect enhanced solubilization of said benzodiazepine, further comprising detecting the enhanced solubilization of said benzodiazepine, and administering the cyclodextrin-benzodiazepine complex thus obtained to said animal.

37. A method for enhancing the availability of a benzodiazepine following administration of a cyclodextrin-benzodiazepine complex to a warm-blooded animal in need of same, said method comprising complexing said benzodiazepine with a cyclodextrin selected from the group consisting of α-cyclodextrin, β-cyclodextrin, γ-cyclodextrin, methylated α-cyclodextrin, methylated β-cyclodextrin, methylated γ-cyclodextrin, hydroxypropyl-α-cyclodextrin, hydroxypropyl-β-cyclodextrin, hydroxypropyl-γ-cyclodextrin, maltosyl-α-cyclodextrin, maltosyl-β-cyclodextrin, maltosyl-γ-cyclodextrin, β-cyclodextrin sulfobutyl ether, hydroxyethyl-β-cyclodextrin, hydroxyethyl-γ-cyclodextrin, α-cyclodextrin carboxymethyl ether, β-cyclodextrin carboxymethyl ether and γ-cyclodextrin carboxymethyl ether, in an aqueous medium at a pH level below about 5 and allowing the resultant complexation medium to equilibrate for sufficient time to effect enhanced solubilization of said benzodiazepine, further comprising administering the cyclodextrin-benzodiazepine complex thus obtained to said animal.

38. A method according to claim 33, wherein the benzodiazepine is alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam or loprazolam.

39. A method according to claim 35, wherein the benzodiazepine is alprazolam, brotizolam, chlordiazepoxide, clobazam, clonazepam, clorazepam, demoxazepam, flumazenil, flurazepam, halazepam, midazolam, nordazepam, medazepam, diazepam, nitrazepam, oxazepam, midazepam, lorazepam, prazepam, quazepam, triazolam, temazepam or loprazolam.

40. A method according to claim 33, wherein the benzodiazepine is complexed with hydroxypropyl-β-cyclodextrin, β-cyclodextrin sulfobutyl ether, β-cyclodextrin, γ-cyclodextrin of hydroxypropyl-γ-cyclodextrin.

41. A method according to claim 35, wherein the benzodiazepine is complexed with hydroxypropyl-β-cyclodextrin, β-cyclodextrin sulfobutyl ether, β-cyclodextrin, γ-cyclodextrin or hydroxypropyl-γ-cyclodextrin.

42. A method according to claim 33, wherein the complexation is conducted at a pH level between about 3 and about 5.

43. A method according to claim 35, wherein the complexation is conducted at a pH level between about 3 and about 5.

44. A method according to claim 35, further comprising formulating the cyclodextrin-benzodiazepine complex thus obtained as an aqueous solution or a hydrogel.

45. A method according to claim 35, wherein said benzodiazepine is selected from the group consisting of midazolam, alprazolam, clonazepam, lorazepam and triazolam and further comprising formulating the cyclodextrin-drug complex thus obtained as an aqueous solution.

46. A method according to claim 45, further comprising formulating the aqueous solution to be at a pH level of below about 4.7 and administering it as a nasal spray.

47. A method according to claim 46, wherein the pH level of the nasal spray is between about 3 and about 4.7.

48. A method according to claim 35, further comprising complexing said benzodiazepine with said cyclodextrin in the presence of from about 0.001 to about 5% (weight/volume) of a pharmacologically inactive, pharmaceutically acceptable water-soluble polymer at a temperature of from about 30° C. to about 150° C.

49. A method according to claim 36, further comprising complexing said benzodiazepine with said cyclodextrin in the presence of from about 0.001 to about 5% (weight/volume) of a pharmacologically inactive, pharmaceutically acceptable water soluble polymer at a temperature of from about 30° C. to about 150° C.

50. A method according to claim 37, further comprising complexing said benzodiazepine with said cyclodextrin in the presence of from about 0.001 to about 5% (weight/volume) of a pharmacologically inactive, pharmaceutically acceptable water-soluble polymer at a temperature of from about 30° C. to about 150° C.

* * * * *